United States Patent [19]

Kojima et al.

[11] Patent Number: 5,538,612
[45] Date of Patent: *Jul. 23, 1996

[54] OXYGEN SENSOR ELEMENT

[75] Inventors: Takao Kojima, Nagoya; Noriaki Kondo, Ichinomiya; Masahiko Yamada, Nagoya, all of Japan

[73] Assignee: NGK Spark Plug Co., Ltd., Nagoya, Japan

[ * ] Notice: The term of this patent shall not extend beyond the expiration date of Pat. No. 5,443,711.

[21] Appl. No.: 837,088

[22] Filed: Mar. 12, 1992

Related U.S. Application Data

[63] Continuation of Ser. No. 429,944, Nov. 1, 1989, abandoned.

[51] Int. Cl.$^6$ ............................................. G01N 27/407
[52] U.S. Cl. ................................. 204/429; 204/426
[58] Field of Search .................... 204/153.18, 421–429

[56] References Cited

U.S. PATENT DOCUMENTS

| | | | |
|---|---|---|---|
| 3,843,400 | 10/1974 | Radford et al. | 204/421 |
| 3,978,006 | 8/1976 | Topp et al. | 204/429 |
| 3,989,614 | 11/1976 | Tien | 204/426 |
| 4,097,353 | 6/1978 | Kishida et al. | 204/429 |
| 4,174,258 | 11/1979 | Bode | 204/429 |
| 4,276,142 | 6/1981 | Topp et al. | 204/429 |
| 4,280,890 | 7/1981 | Friese et al. | 204/421 |
| 4,720,335 | 1/1988 | Fukushima et al. | 204/424 |
| 4,915,080 | 4/1990 | Nakaniwa et al. | 204/426 |

FOREIGN PATENT DOCUMENTS

| | | |
|---|---|---|
| 55-20423 | 2/1980 | Japan . |
| 2200460 | 8/1988 | United Kingdom . |

OTHER PUBLICATIONS

Hackh's Chemical Dictionary, 4th ed. (1969) month unavailable, p. 687.

*Primary Examiner*—T. Tung
*Attorney, Agent, or Firm*—Fish & Richardson

[57] ABSTRACT

An oxygen sensor element comprises a reference-gas-side electrode on one surface of a solid electrolyte having oxygen-ion conductivity, a detection-gas-side electrode on another surface, and a porous coated layer formed of a heat-resistant metal oxide formed on the surface of the detection-gas-side electrode, wherein at least a part of said coated layer is formed of a nonstoichiometric compound of transition metal (Ti, Co, Ni) oxide, and a portion formed of said nonstoichiometric compound carries a catalyst for equilibrating gas components of a detection gas. The catalyst (Pt, Rh) is 0.2–5 mole % relative to the portion formed of said nonstoichiometric compound. The coated layer may be thickened at the distal end portion.

27 Claims, 7 Drawing Sheets

OXYGEN SENSOR ELEMENT

This application is a continuation of U.S. application Ser. No. 07/429,944 filed Nov. 1, 1989, now abandoned.

FIELD OF THE INVENTION

This invention relates to an oxygen sensor element used in an oxygen sensor for measuring oxygen concentration in exhaust gases in order to perform purification of exhaust engine and gases of, for example, an internal combustion various kinds of combustion machines and the like.

BACKGROUND

Heretofore, there have been used oxygen sensors for detecting oxygen concentration in exhaust gases in order to purify exhaust gases by controlling the air-to-fuel ratio of an internal combustion engine, various combustion machines and the like.

The oxygen sensor produces an electromotive force in accordance with the difference between the oxygen concentration in a detection gas, such as an exhaust gas and the like, and the oxygen concentration in a reference gas. Since the electromotive force abruptly changes at the point of the theoretical air-to-fuel ratio, the air-to-fuel ratio of the detection gas can be obtained by measuring the electromotive force.

As the oxygen sensor element used for the above-described oxygen sensor, there is a sensor element in which electrodes are provided at both surfaces of an oxygen-ion-conductive solid electrolyte consisting of, for example, zirconia. One of the electrodes is exposed to the detection-gas side, and another electrodes is exposed to the reference-gas side.

There have been developed techniques for protecting the electrode at the detection-gas side of the above-described oxygen sensor element, and promoting the oxidation reaction of gas components, such as, CO, HC, $H_2$ and the like, performed at the electrode to detect the air-to-fuel ratio with an excellent accuracy. There has been proposed, for example, an oxygen sensor in which a porous second coated layer is formed on the surface of the detection-gas-side electrode using $Al_2O_3$, and a first coated layer is formed on the surface of the second coated layer using $Al_2O_3$ which carries a Pt catalyst for promoting oxidation reaction (refer to JP Patent Kokoku Publication No. 57-34900 (1982)).

Problems to be Solved by the Invention

However, when the first coated layer is formed using $Al_2O_3$ carrying the Pt catalyst, there have been problems that the responsive property of the oxygen sensor decreases caused by (a) excessive adsorption of gas components of the detection gas on Pt having a high catalytic property, and (b) penetration of Pt fine particles into minute pores of the coated layer to produce blocking (or plugging) of the pores and the like. If the amount of the Pt catalyst to be carried is reduced in order to solve the above-described problem, Pt dissipates while being used, and hence there arises a new problem that the effect as a catalyst decreases.

SUMMARY OF THE DISCLOSURE

It is an object of the present invention to provide a novel oxygen sensor element freed of the above-described problems.

According to the present invention there is provided an oxygen sensor element comprising a reference-gas-side electrode on one surface of a solid electrolyte having oxygen-ion conductivity and a detection-gas-side electrode on another surface, said detection-gas-side electrode having a first porous coated layer wherein at least a part of the coated layer comprises a nonstoichiometric compound of a transition metal oxide, and an oxidizing catalyst for equilibrating gas components of a detection gas.

As the above-described nonstoichiometric compound of the transition metal oxide, titanium oxide as well as cobalt oxide, nickel oxide and the like can be used. As the above-described catalyst carried by the nonstoichiometric compound of the transition metal oxide, Pt can be used. Especially when the carried amount of Pt is not less than 0.2 mole % and not more than 5 mole % relative to the nonstoichiometric compound of the transition metal oxide, catalystic effect is satisfactory, and responsive property is also excellent. Hence, an excellent oxygen sensor element can be provided.

It is preferred that the catalyst in the above-described coated layer is carried in the nonstoichiometric compound of the transition metal oxide and also in other portions of the coated layer. The nonstoichiometric compound of the transition metal oxide may also be formed on the entire surface layer of the coated layer. The entire coated layer may also be formed of the nonstoichiometric compound of the transition metal oxide.

In the oxygen sensor element of the present invention, electrodes are formed on both sides of an oxygen-ion-conductive solid electrolyte, and a coated layer of porous heat-resistant metal oxide is formed on the surface of a detection-gas-side electrode.

In addition, since at least a part of the coated layer is formed of a nonstoichiometric compound of a transition metal oxide and carries a catalyst for equilibrating gas components of a detection gas, the equilibration of the oxidatation reaction of the gas components is promoted.

Furthermore, since the nonstoichiometric compound has properties of removing excessive oxygen within the gas and releasing oxygen into the gas due to variations of electrons and holes in accordance with the amount of oxygen, it is possible to complement the oxidation reaction and prevent excessive adsorption of the gas components on the carried catalyst.

The oxidation reaction is thereby securely performed, and the responsive property is also improved.

As explained above, in the oxygen sensor according to the present invention, since the first porous coated layer is formed at least on the surface of a detection-gas-side electrode of the oxygen-ion-conductive solid electrolyte, the electrode is protected from obstructions due to adherence of carbon, peeling and the like. Furthermore, since the coated layer is provided with the nonstoichiometric compound of transition metal oxide carrying the catalyst, the oxidation reaction of gas components within a detection gas can be sufficiently performed, and the responsive property can also be increased. In addition, blocking of pores due to action of the catalyst does not occur, and decrease in the oxidation reaction of the oxygen sensor due to dissipation of the catalyst and decrease in durability due to adsorption of gases are not caused.

DESCRIPTION OF THE PREFERRED EMBODIMENTS

As the above-described two electrodes, Pt, Pt-Rh alloy, Rh and the like, are, for example, used, and as the material for the portion other than the nonstoichiometric compound of the transition metal oxide of the coated layer, spinel, $Al_2O_3$ and the like, are, for example, used.

Furthermore, in order to promote equilibration of the detection gas especially at low temperatures, the layer of spinel, $Al_2O_3$ or the like formed on the surface of the detection-gas-side electrode may be thickened at a distal end portion of the oxygen sensor element, and the catalyst may be carried at the distal end portion. In addition, the distal end portion may be thickened by forming a protective layer of another metal oxide (for example, an $Al_2O_3$ layer) on the surface of the spinel.

The nonstoichiometric compound of transition metal oxide can be formed by heating (400°–500° C.) transition metal oxide such as titania ($TiO_2$) in a reducing atmosphere or by heating under the presence of catalyst such as Pt resulting in a state of less oxygen than the stoichiometric oxide, e.g., $TiO_{2-x}$, where x is generally $0<x\leq0.4$, preferably $0.02\leq x\leq0.2$. The transition metal is preferably Ti, Co and/or Ni, most preferably Ti.

Under the presence of Pt, the titanium oxide is in the nonstoichiometric state at temperatures of about 900° C. or below in a gas containing a small amount of oxygen (e.g., not exceeding 4%). In the atmospheric air containing more oxygen the nonstoichiometric state is kept below about 700° C. Such nature should be observed when the oxygen sensor element is used.

EXAMPLES

Embodiments of the present invention will be hereinafter explained with reference to the drawings.

Example 1

Figure 1:
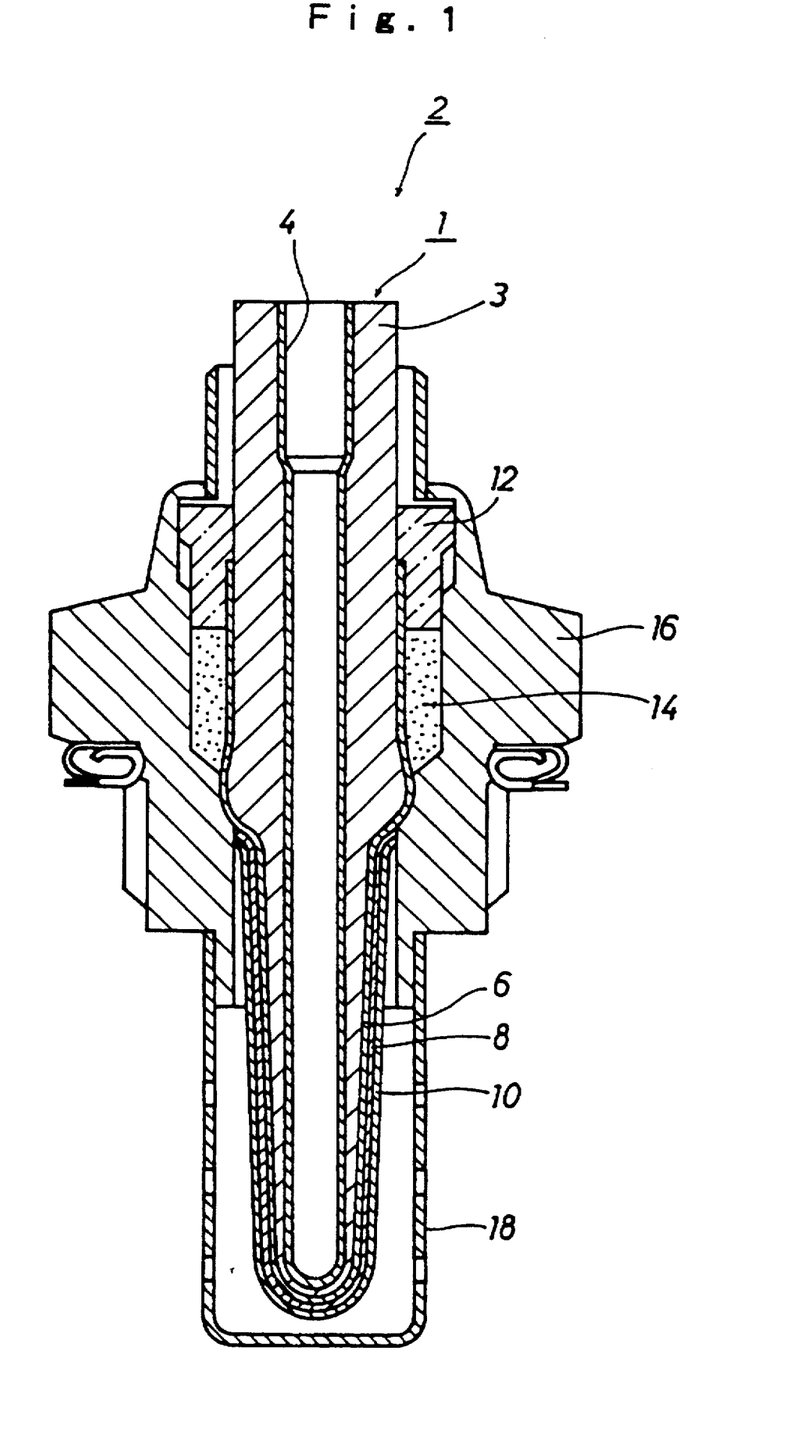
FIG. 1 is a cross-sectional view showing an oxygen sensor of a first embodiment of the present invention.
Figure 2:
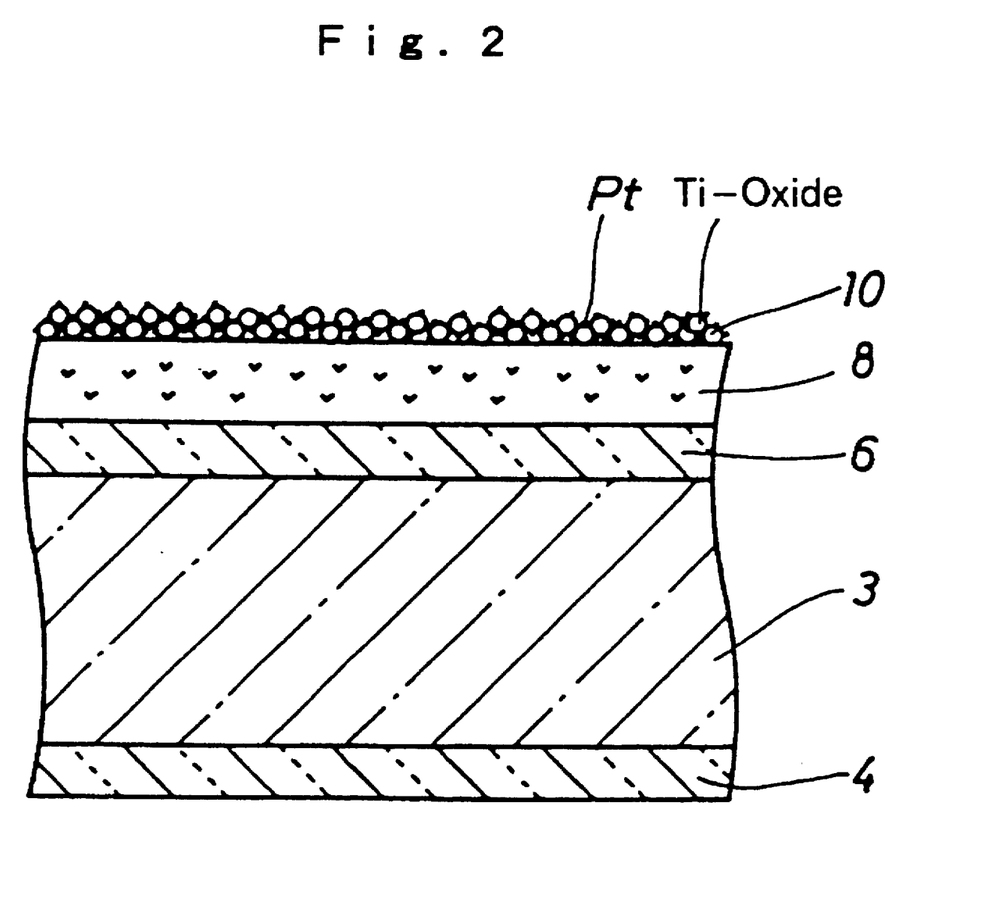
FIG. 2 is a partially enlarged view showing a cross section of the distal end of an oxygen sensor element for the oxygen sensor.

FIG. 1 shows an oxygen sensor 2 provided with an oxygen sensor element 1 of a first embodiment. FIG. 2 is a partially enlarged view of the distal end of the oxygen sensor element 1.

As shown in FIG. 1, a solid electrolyte 3 of the oxygen sensor element 1 made of stabilized or partially-stabilized zirconia having oxygen-ion conductivity is formed in the shape of a test tube, and is provided with platinum (Pt) electrodes 4 and 6 on its inner side (the reference-gas side) and outer side (the detection-gas side), respectively.

As shown in FIG. 2, a second coated layer 8 consisting of spinel ($Al_2O_3$.MgO) is formed on the surface of the electrode 6 on the detection-gas side, and a first coated layer 10 consisting of nonstoichiometric titanium oxide carrying a Pt catalyst is further formed on the surface of the second coated layer 8.

As shown in FIG. 1, the oxygen sensor element 1 is fixed to a housing 16 made of stainless steel by a ring 12 and a filler powder 14. A protective tube 18 coveres the distal end of the oxygen sensor element 1.

Next, the production method of the oxygen sensor element 1 will be explained.

First, 4 mole % of $Y_2O_3$ having a 99.9% purity is added to $ZrO_2$ raw material having a 99% purity. The resultant mixture is subjected to wet grinding and blending, and then calcined at 1300° C. for 2 hours.

The calcined material is then subjected to wet grinding until 80% of particles achieve a particle size of not more than 2.5 μm. A water-soluble binder is added to the ground material, and spherical secondary particles (granules) having an average granule size of about 70 μm are formed by a spray dryer. The resultant granules are then formed into a predetermined shape of a test tube as shown in FIG. 1, and fired at about 1500° C. to form a solid electrolyte body 3.

Subsequently, Pt is chemically plated on the surface of the solid electrolyte body 3, which is then subjected to heat treatment, and a detection-gas-side electrode 6 and a reference-gas-side electrode 4 are formed.

Subsequently, as shown in FIG. 2, spinel is flame-sprayed by plasma on the surface of the detection-gas-side electrode 6 to form a second coated layer 8 about 100 μm thick having many minute pores. Alternatively this porous layer may be formed by coating a paste of granular or coarse spinel particles followed by heating.

Subsequently, a titanium oxide powder ($TiO_{2-x}$, where $0.02\leq x\leq0.2$) as a nonstoichiometric compound of a transition metal oxide is impregnated with aqueous $H_2PtCl_6$ solution or Pt black dispersed in an organic solvent in an impregnated Pt amount of not less than 0.2 mole % and not more than 5 mole % of Pt, and then dried.

Subsequently, the dried titanium oxide powder is subjected to heat treatment in $N_2$ atmosphere, and butyl carbidol and an organic binder are added thereto to provide a paste. By coating the paste on the surface of the second coated layer 8 and performing firing, a first coated layer 10 about 25 μm thick having minute pores (about 10 μm or less) is formed.

By the above-described steps, the oxygen sensor element 1, in which the detection-gas-side electrode 6, the second coated layer 8 and the second coated layer 10 are successively laminated on the solid electrolyte body 3, is formed.

Next, experiments performed using the measuring apparatus shown in FIG. 3 in order to confirm improvement in responsive property among effects of the oxygen sensor element 1 of the present embodiment will be explained.

EXPERIMENTAL DATA (1)

Figure 3:
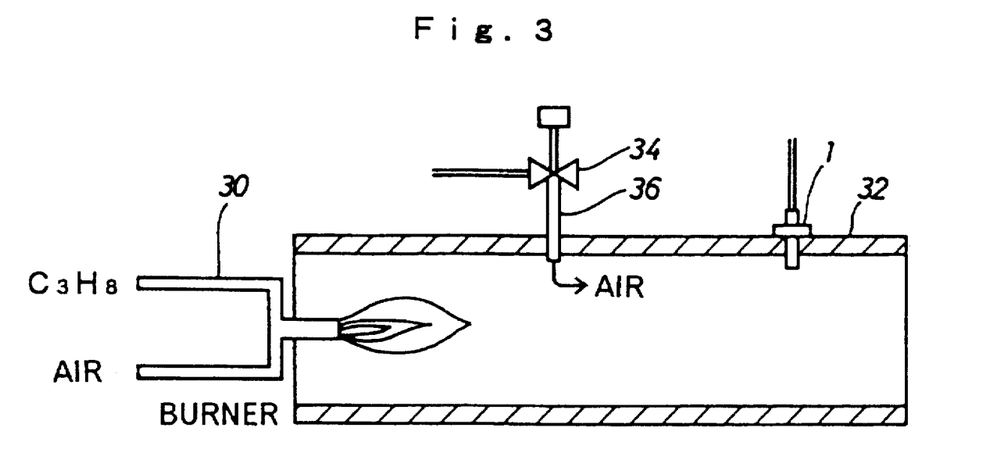
FIG. 3 is a schematic configurational diagram showing an experimental apparatus for measuring the performance of the oxygen sensor.

The measuring apparatus shown in FIG. 3 in which air and $C_3H_8$ are mixed with a weight ratio of air:$C_3H_8$=22:1 (a fuel-rich state) and burnt within an exhaust pipe 32 by a main burner 30 is used. An air intake 36 opened and closed by a solenoid valve 34 is provided at an intermediate of the exhaust pipe 32 to perform introduction and stop of introduction of air. The oxygen sensor 2 provided with the present oxygen sensor element 1 is mounted at the downstream side 30 cm from the air intake 36, and the output of the oxygen sensor 2 is measured at the flow rate of 10 m/s of an exhaust gas.

Figure 4:
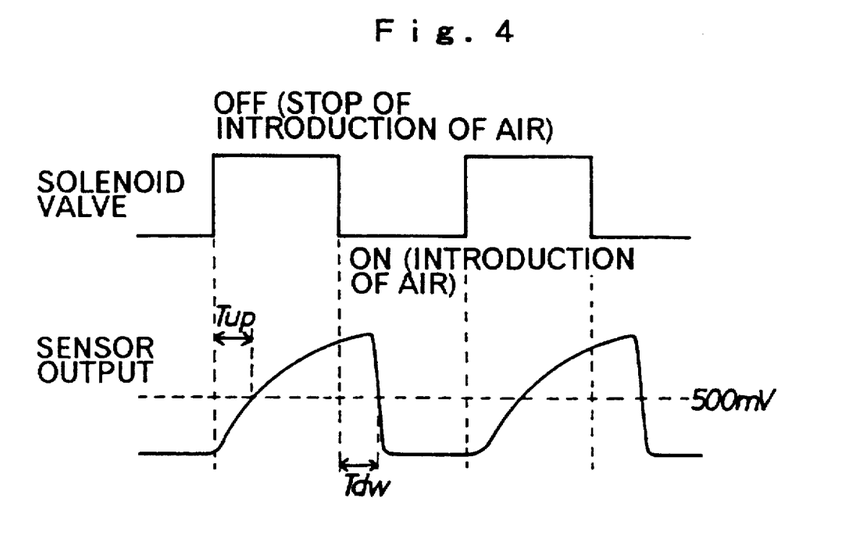
FIG. 4 is an explanatory diagram showing the output of the oxygen sensor.

As shown in FIG. 4, introduction or the stop of introduction of air was performed by switching on or off the solenoid valve 34, and the rise response time $T_{up}$ (ms) and the fall response time $T_{dw}$ (ms) until the output of the oxygen sensor 2 becomes 500 mV from switching time on and off of the solenoid valve 34, respectively, were measured.

In addition, as a durability test, after being burnt at the burning temperature of 900° C. for 100 hours, the rise response time $T_{up}$ and the fall response time $T_{dw}$ were measured again by the above-described measuring apparatus.

As to the oxygen sensor 2 used for the experiments, the experiments were performed with changing the amount of Pt in $H_2PtCl_6$ and Pt black and also whether or not heat treatment was performed. The conditions of the experiments and the results of the experiments are shown in Table 1.

In Table 1, Nos. 1–8 are First Examples when nonstoichiometric titanium oxide was used as the first coated layer 10. Comparative Example Nos. 9 and 10 are examples when the first coated layer 10 was not formed, and Comparative Example Nos. 11–14 are examples when $Al_2C_3$, in which 50% of the particles had particle sizes of not more than 7 μm, was used instead of the titanium oxide. The magnification indicated in Table 1 represents comparative data making the rise response time $T_{up}$ and the fall response time $T_{dw}$ relative to a reference value=1 for the Comparative Example No. 9, respectively. The responsive property of Comparative Example No. 9 is excellent because it does not carry the Pt catalyst, but this sample can not sufficiently perform oxidation reaction.

As is apparent from the data of magnification at the first measurement and the measurements after 100 hours in Table 1, the rise response times $T_{up}$ in First Example Nos. 1–8 are not more than 1.10 and the fall response times $T_{dw}$, are not more than 0.9. These values indicate very excellent response properties. In addition, the samples show excellent response properties when the carried amounts of the Pt catalyst are not less than 0.2 mole % and not more than 5 mole %.

Accordingly, the following facts have become evident from the above-described experiments.

When the amount of the Pt catalyst carried in the nonstoichiometric titanium oxide is not less than 0.2 mole % and not more than 5 mole %, adsorption of gas components on the Pt catalyst is little, and the responsive property is excellent.

Furthermore, when the amount of the Pt catalyst is within the above-described range, blocking of the pores due to the Pt or the action of the Pt catalyst hardly occurs, and the phenomenon that the Pt amount decreases through dissipation entailing disappearance of the catalytic effect does not occur either.

That is, by using the nonstoichiometric compound of a transition metal oxide, the amount of the carried catalyst can be reduced compared with the conventional oxygen sensors, and accordingly blocking due to the action of the catalyst does not occur.

In addition, since the responsive property is improved by using a nonstoichiometric compound of the transition metal oxide, it is unnecessary to excessively reduce the amount of the carried catalyst in order to improve the responsive property, and accordingly a decrease in the oxidation reaction of the oxygen sensor due to dissipation of the catalyst is not caused either.

Example 2

Figure 5:
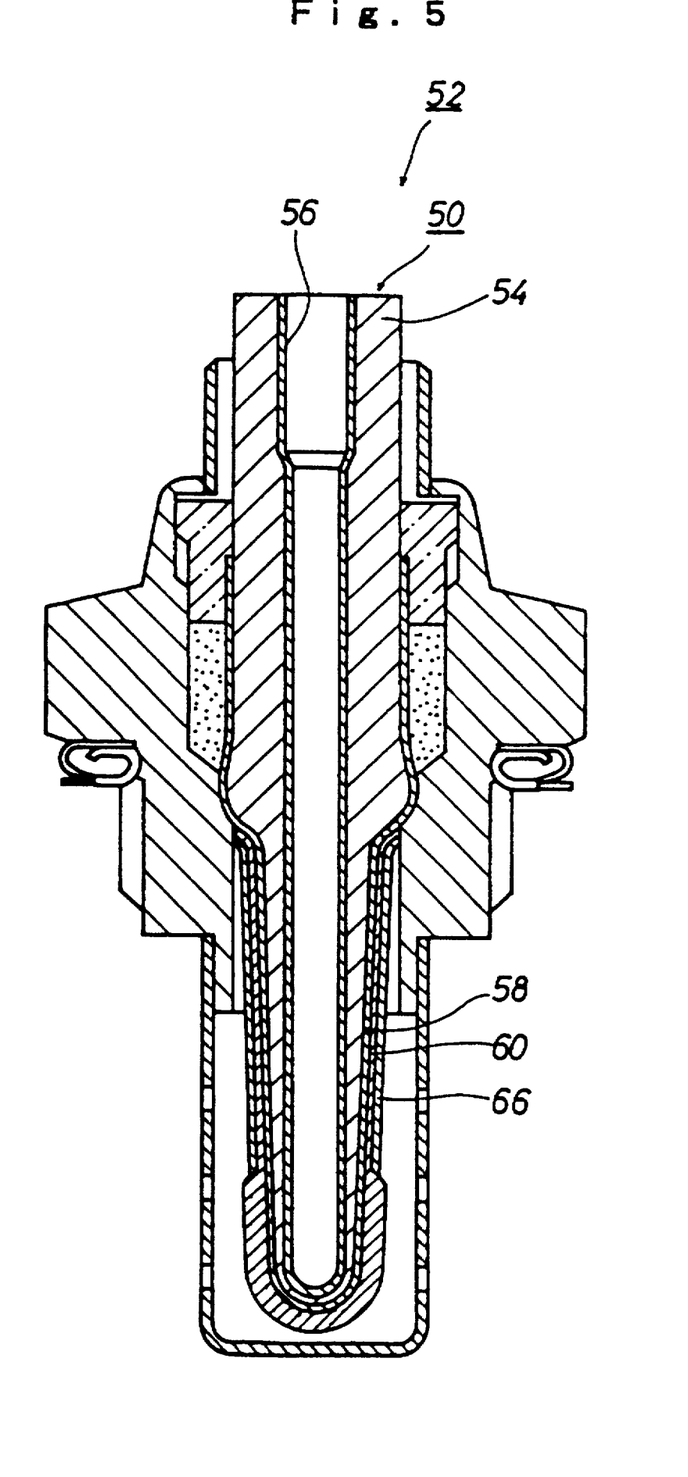
FIG. 5 is a cross-sectional view showing an oxygen sensor of a second embodiment of the present invention.
Figure 6:
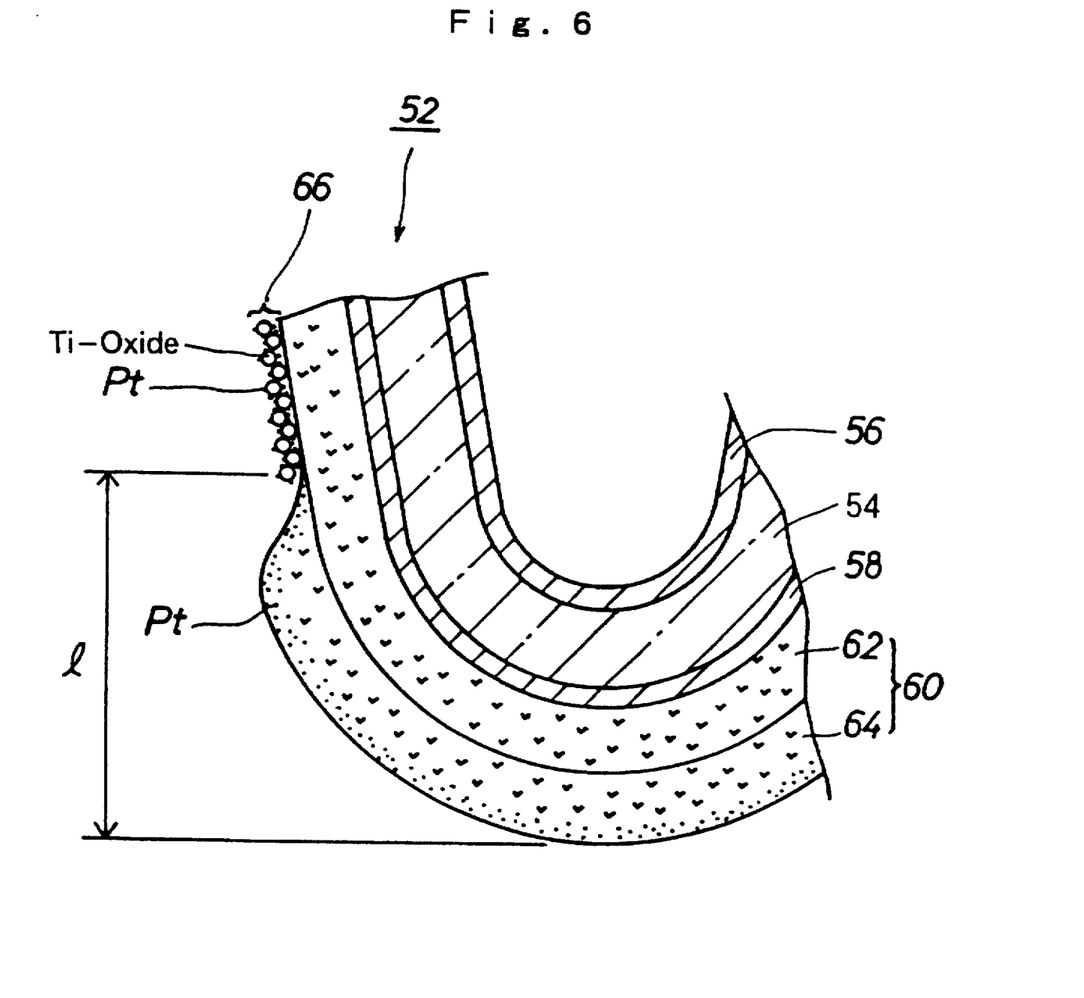
FIG. 6 is a partially enlarged view showing a cross section of the distal end of an oxygen sensor element for the oxygen sensor in FIG. 5.

Next, a second embodiment of the present invention will be explained. FIG. 5 shows an oxygen sensor 52 provided with an oxygen sensor element 50 of the second embodiment. FIG. 6 is a partially enlarged view of the distal end of the oxygen sensor element 50.

As in the first embodiment, the oxygen sensor element 50 is provided with Pt electrodes 56 and 58 of the reference-gas side and the detection-gas side on each side of an oxygen-ion-conductive solid electrolyte 54, respectively. A double coated layer 60 consisting of spinel is formed on the surface of the detection-gas-side electrode 58. The double coated layer 60 is formed of a thin-layer portion 62 as a primary or second porous coated layer on the side of the electrode 58 and a surface-layer portion 64 as an outer porous coated layer laminated on the surface the thin-layer portion 62.

As shown in FIG. 6, the surface-layer portion 64 is laminated on a part of the surface of the thin-layer portion 62 within a range of thickness w of not less than 50 μm and not more than 150 μm, and within a range of the length l from the distal end of the oxygen sensor element 50 of not less than ⅕ and not more than ½ of the double coated layer 60. Furthermore, Pt is carried at near the surface of the surface-layer portion 64.

On the other hand, on the surface of the thin-layer portion 62 on which the surface-layer portion 64 is not laminated, a first coated layer 66 consisting of nonstoichiometric titanium oxide carrying the Pt catalyst is formed.

Next, the production method of the oxygen sensor element 50 of the present embodiment will be explained.

First, as in the first embodiment, the solid electrolyte 54 and the two electrodes 56 and 58 are produced.

Spinel is then flame-sprayed by plasma on the surface of the detection-gas-side electrode 58 to form the thin-layer portion 62 about 100 μm thick. The surface-layer portion 64 is then formed within the above-described ranges of the thickness w and the length l on the surface of the thin-layer portion 62 in the same manner.

The surface-layer portion 64 is then immersed in an aqueous solution of $H_2PtCl_6$ having a Pt concentration of 5 g/l, and Pt is impregnated for about 5 minutes with evacuating in about 300 mmHg.

Subsequently, on the surface of the thin-layer portion 62 on which the surface-layer portion 64 is not formed, a layer of titanium oxide 25 μm thick as a nonstoichiometric compound of a transition metal oxide carrying the Pt catalyst is formed as in the first embodiment.

Next, experiments performed in order to confirm improvements in output range, shift of air-to-fuel ratio and control frequency Hz, among effects of the oxygen sensor element 50 of the present embodiment will be explained.

EXPERIMENTAL DATA (2)

The oxygen sensor 52 provided with the oxygen sensor element 50 was mounted to an exhaust pipe of a multicylinder engine (not shown), and tile air-to-fuel ratio of the engine was controlled according to the output of the oxygen sensor 52.

The engine was set to 800 r.p.m., and the output range (mV) of the oxygen sensor 52 when the temperature of the exhaust gas is low was measured. The controlled air-to-fuel ratio while driving at 80 km/hr was measured as data for high revolution of the engine. Control frequency (Hz) in that state was also measured.

Figure 7A:
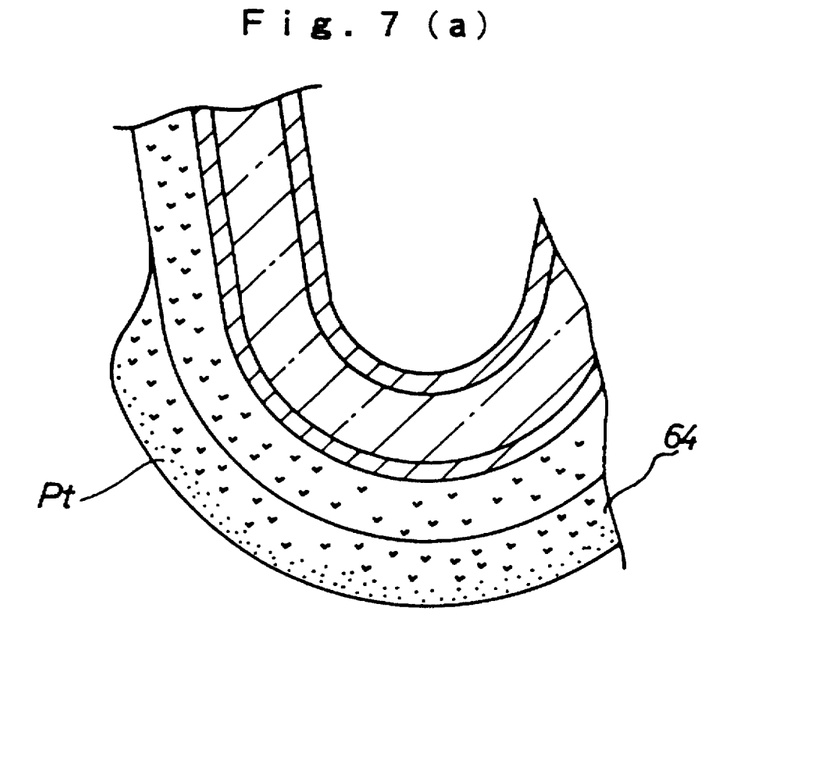
FIG. 7 is a cross-sectional view of an oxygen sensor element used for comparison to the second experiment.
Figure 7B:
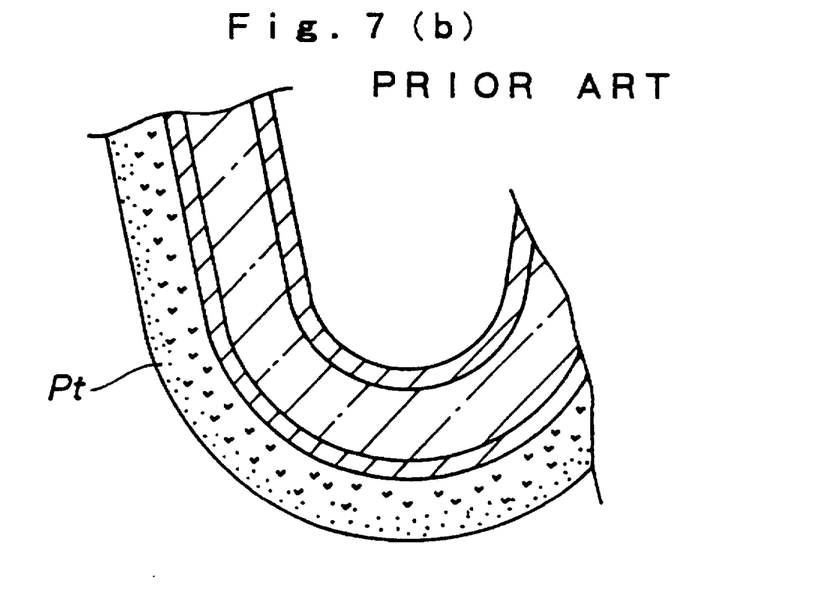

As the oxygen sensor 52 used for the experiments, various oxygen sensors as shown in Table 2 were used. In Table 2, the oxygen sensor 52 of the second embodiment was used in Second Example Nos. 1–10, and the thickness w and the length l of the surface-layer portion 64 were varied within the ranges described above. Nos. 11–16 are Comparative Examples in which the thickness w and the length l of the surface-layer portion 64 were varied outside the above-described ranges. The Sample No. 17 has the surface-layer portion 64 carrying the Pt catalyst, but does not have the first coated layer 66 of the nonstoichiometric compound (FIG. 7(a)). Namely Sample No. 17 is such that the nonstoichiometric compound is removed from Sample No. 7. The Sample No. 18 is a conventional example which neither has the surface-layer portion 64 nor the first coated layer 66 of the nonstoichiometric compound (FIG. 7(b)).

The results of the experiments are shown in Table 2.

As is apparent from Table 2, using the oxygen sensor element 50 in which the surface-layer portion 64 is within the range of the above-described embodiment, the output range of the oxygen sensor 52 when the temperature of the exhaust gas is low also becomes large. Furthermore, shift in controlled air-to-fuel ratio at high revolution of the engine is small, and delay in the control frequency Hz is also small. Hence, preferable results have been obtained. It is considered that these results are attributable to the following reasons.

That is, when the revolution of a multicylinder engine of an automobile and the like is low, that is, when the temperature of the exhaust gas is low, the concentration of the detection gas component in the exhaust gas varies due to variations in combustion of cylinders, and a so-called turbulence (chemical noise) is sometimes produced. When the temperature of the exhaust gas is low, the turbulence usually flows through the central portion of the exhaust pipe. Hence, the detection gas in the exhaust gas reaches the thick portion at the distal end portion of the oxygen sensor element 50, that is, the surface-layer portion 64 and the thin-layer portion 62, and is sufficiently mixed within these layers. The concentration of the detection gas component is thus equalized, and equilibration is promoted. Since it becomes thereby difficult to pick up noise due to the turbulence and a decrease in output due to variations in concentration is also small, the output range of the oxygen sensor 52 becomes large. Accordingly, the control of air-to-fuel ratio according to the output of the oxygen sensor 52 can be properly performed. On the other hand, when the revolution of the engine is high, there are the functions and effects as described above due to nonstoichiometric titanium oxide carrying the Pt catalyst. Accordingly, control can be successfully performed because shift in air-to-fuel ratio is small, and the frequency controlling air-to-fuel ratio (control frequency Hz) does not suffer delay.

It is to be noted that, as another embodiment in which the double coated layer 60 becomes thick at the distal end of the oxygen sensor element 50, the kinds or concentrations of the catalyst in the surface-layer portion 64 and the catalyst in the first coated layer 66 may be different from each other. Furthermore, in order to promote the catalytic reaction of the exhaust gas at low temperatures, a highly reactive Rh catalyst may be used for the surface-layer portion 64.

Figure 8:
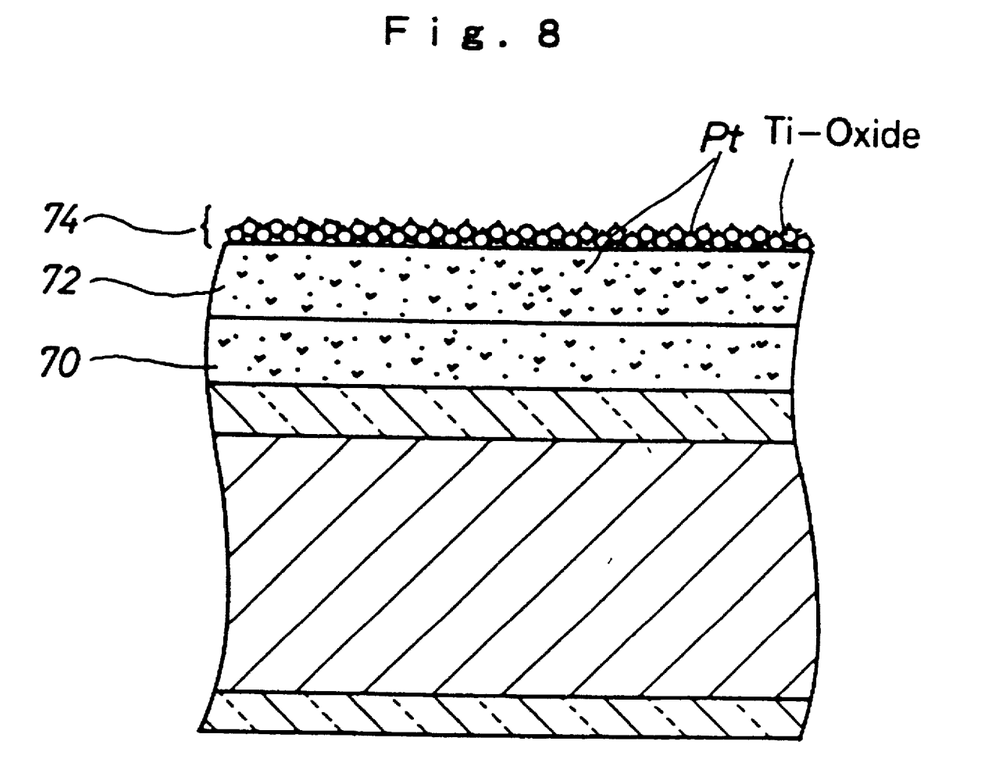
FIG. 8 is a cross-sectional view of another embodiment of the present invention.

Moreover, as shown in FIG. 8, a layer 74 of titanium suboxide carrying the Pt catalyst may be formed also on a surface-layer portion 72 in addition to a thin-layer portion 70. In addition, the Pt catalyst may also be carried on the surface layer portion 72 and the thin-layer portion 70. The layer portions 70 and 72 can replace the second coated layer 8 of FIG. 2.

Although, in the above-described embodiments, spinel was used for the second coated-layer 8 or the double coated layer 60, other materials, such as $Al_2O_3$ and the like, may also be used.

It should be noted that modification may be made without departing from the gist and concept of the present invention as herein disclosed within the scope as defined in the appended claims.

TABLE 1

| Examples No. Experimental Data (1) | Material for 1st coated layer | Amount of $H_2PtCl_6$ (mole %) | Heat treatment | Amount of Pt black (mole %) | Results of 1st measurement | | | | Results of measurement after 100 hours | | | | Suitable or not |
|---|---|---|---|---|---|---|---|---|---|---|---|---|---|
| | | | | | $T_{up}$ [ms] | $T_{dw}$ [ms] | Magnification relative to comparative Example No. 9 | | $T_{up}$ [ms] | $T_{dw}$ [ms] | Magnification relative to comparative Example No. 9 | | |
| | | | | | | | $T_{up}$ | $T_{dw}$ | | | $T_{up}$ | $T_{dw}$ | |
| First Examples | | | | | | | | | | | | | |
| 1 | Ti-oxide | 1 | YES | — | 91 | 60 | 1.01 | 0.75 | 93 | 66 | 1 | 0.87 | YES |
| 2 | ↑ | 3 | YES | — | 92 | 58 | 1.02 | 0.73 | 94 | 63 | 1.01 | 0.83 | YES |
| 3 | ↑ | 5 | YES | — | 95 | 68 | 1.09 | 0.85 | 98 | 67 | 1.05 | 0.88 | YES |
| 4 | ↑ | 0.2 | — | — | 90 | 60 | 1 | 0.75 | 93 | 65 | 1 | 0.86 | YES |
| 5 | ↑ | 0.5 | — | — | 91 | 59 | 1.01 | 0.74 | 96 | 63 | 1.01 | 0.83 | YES |
| 6 | ↑ | 0.7 | — | — | 94 | 59 | 1.04 | 0.74 | 96 | 63 | 1.03 | 0.83 | YES |
| 7 | ↑ | 2.5 | — | — | 97 | 65 | 1.08 | 0.81 | 101 | 67 | 1.08 | 0.88 | YES |
| 8 | ↑ | 1 | YES | 2 | 96 | 67 | 1.08 | 0.84 | 102 | 65 | 1.10 | 0.86 | YES |
| Comparative Examples | | | | | | | | | | | | | |
| 9 | — | — | — | — | 90 | 80 | 1 | 1 | 93 | 76 | 1 | 1 | NO |
| 10 | — | 1 | — | — | 107 | 90 | 1.19 | 1.13 | 117 | 63 | 1.26 | 0.83 | NO |

TABLE 1-continued

| Examples No. Experimental Data (1) | Material for 1st coated layer | Amount of $H_2PtCl_6$ (mole %) | Heat treatment | Amount of Pt black (mole %) | Results of 1st measurement | | | | Results of measurement after 100 hours | | | | Suitable or not |
|---|---|---|---|---|---|---|---|---|---|---|---|---|---|
| | | | | | $T_{up}$ [ms] | $T_{dw}$ [ms] | Magnification relative to comparative Example No. 9 | | $T_{up}$ [ms] | $T_{dw}$ [ms] | Magnification relative to comparative Example No. 9 | | |
| | | | | | | | $T_{up}$ | $T_{dw}$ | | | $T_{up}$ | $T_{dw}$ | |
| 11 | $Al_2O_3$ | 1 | — | — | 94 | 75 | 1.04 | 0.94 | 92 | 76 | 0.99 | 1 | NO |
| 12 | ↑ | 1 | YES | — | 92 | 78 | 1.02 | 0.98 | 94 | 76 | 1.01 | 1 | NO |
| 13 | ↑ | 1 | YES | 2 | 98 | 82 | 1.09 | 1.03 | 106 | 86 | 1.14 | 1.13 | NO |
| 14 | ↑ | 3 | YES | — | 96 | 70 | 1.07 | 0.88 | 105 | 65 | 1.13 | 0.86 | NO |

TABLE 2

| Examples No. Experimental Data (2) | Length l of surface layer Length of 2nd coated layer | Thickness w of surface layer (μm) | (1) Output range of sensor at 800 rpm idling (mV) | (2) Controlled air-to-fuel ratio at 80 km/hr driving (A/F) | (3) Control Hz at 80 km/hr driving | Evaluation of measured of values | | | Total evaluation Suitable or not |
|---|---|---|---|---|---|---|---|---|---|
| | | | | | | (1) | (2) | (3) | |
| Second Examples | | | | | | | | | |
| 1 | 1/5 | 100 | 350–700 | 14.55 | 1.93 | ○ | ○ | ○ | YES |
| 2 | 1/3 | ↑ | 300–750 | 14.56 | 1.89 | ○ | ○ | ○ | YES |
| 3 | 2/5 | ↑ | 300–800 | 14.56 | 1.88 | ○ | ○ | ○ | YES |
| 4 | 1/2 | ↑ | 250–850 | 14.57 | 1.83 | ○ | ○ | ○ | YES |
| 5 | 1/3 | 50 | 350–700 | 14.55 | 2.00 | ○ | ○ | ○ | YES |
| 6 | 1/3 | 70 | 320–750 | 14.56 | 1.94 | ○ | ○ | ○ | YES |
| 7 | 1/3 | 130 | 300–780 | 14.57 | 1.85 | ○ | ○ | ○ | YES |
| 8 | 1/3 | 110 | 280–800 | 14.57 | 1.81 | ○ | ○ | Δ | YES |
| 9 | 2/5 | 50 | 350–700 | 14.56 | 1.96 | ○ | ○ | ○ | YES |
| 10 | 2/5 | 150 | 280–830 | 14.58 | 1.78 | ○ | Δ | Δ | YES |
| Comparative Examples | | | | | | | | | |
| 11 | 1/6 | 100 | 400–650 | 14.55 | 2.01 | X | ○ | ○ | NO |
| 12 | 3/5 | ↑ | 230–850 | 14.58 | 1.76 | ○ | Δ | X | NO |
| 13 | 2/3 | ↑ | 230–850 | 14.59 | 1.66 | ○ | X | X | NO |
| 14 | 1/3 | 30 | 400–680 | 14.55 | 2.03 | X | ○ | ○ | NO |
| 15 | 1/3 | 170 | 250–830 | 14.59 | 1.68 | ○ | X | X | NO |
| 16 | 2/5 | 200 | 250–850 | 14.59 | 1.63 | ○ | X | X | NO |
| 17 | without 1st coated layer | | 250–800 | 14.57 | 1.70 | ○ | ○ | X | NO |
| Conventional Example 18 | without surface layer and 1st coated layer | | 400–680 | 14.60 | 2.08 | X | X | ○ | NO |

○: Excellent
Δ: Satisfactory
X: Unsuitable

What is claimed is:

1. An oxygen sensor element comprising a reference-gas-side electrode on one surface of a solid electrolyte having oxygen-ion conductivity and a detection-gas-side electrode on another surface, said detection-gas-side electrode having a first porous coated layer, wherein said first porous coated layer comprises a nonstoichiometric compound of a transition metal oxide and an oxidizing catalyst for equilibrating gas components of a detection gas.

2. The oxygen sensor element according to claim 1, wherein at least a part of said first porous coated layer is formed of a nonstoichiometric compound of a transition metal oxide, and said part formed of said nonstoichiometric compound carries the oxidizing catalyst.

3. The oxygen sensor element according to claim 1 or 2, wherein the oxidizing catalyst is Pt which is carried by said nonstoichiometric compound of the transition metal oxide, and said Pt is present in an amount of 0.2–5 mole % relative to said nonstoichiometric compound.

4. The oxygen sensor element according to claim 2, wherein said part formed of the nonstoichiometric compound is a part of the surface of said first porous coated layer.

5. The oxygen sensor element according to claim 2, wherein said part formed of the nonstoichiometric compound occupies at least a portion of the sensor element which is to be exposed to the detection gas.

6. The oxygen sensor element according to claim 5, wherein the sensor element is of a tubular shape with a closed end, and said part formed of the nonstoichiometric compounds extends over the closed end of the sensor element.

7. The oxygen sensor element according to claim 5, wherein the sensor element is of a tubular shape with a closed end, and said part formed of the nonstoichiometric compound extends over the sensor element except for the closed end.

8. The oxygen sensor element according to claim 1 or 2, wherein said nonstoichiometric compound is at least one material selected from the group consisting of suboxides of Ti, Ni and Co.

9. The oxygen sensor element according to claim 8, wherein said nonstoichiometric compound is a suboxide of Ti.

10. The oxygen sensor element according to claim 1 or 2, wherein a distal end portion of the sensor element is covered by a second porous coated layer carrying an oxidizing catalyst for equilibrating gas components of a detection gas.

11. The oxygen sensor element according to claim 10, wherein the nonstoichiometric compound is titanium suboxide represented by the formula $TiO_{2-x}$ wherein $0.02 \leq x \leq 0.4$ and the oxidizing catalyst is 0.2–5 mole % Pt relative to the nonstoichiometric compound.

12. The oxygen sensor element according to claim 2, wherein the titanium suboxide is represented by the formula $TiO_{2-x}$, wherein $0 < x \leq 0.4$.

13. The oxygen sensor element according to claim 12, wherein $0.02 \leq x \leq 0.4$.

14. The oxygen sensor element according to claim 12, wherein $0.02 \leq x \leq 0.2$.

15. The oxygen sensor element according to claim 1 or 2, wherein said nonstoichiometric compound has a nonstoichiometry sufficient to perform an oxidation reaction of gas components in cooperation with the oxidizing catalyst within a detection gas.

16. The oxygen sensor element according to claim 1 or 2, wherein said sensor element has a reduced shift amount of the control point of excess air factor in terms of fall down time Tdw by a factor of at least 0.1 over a sensor element having the same structure except that a stoichiometric compound of a transition metal is used instead of said nonstoichiometric compound.

17. The oxygen sensor element according to claim 16, wherein said reduction in shift amount of the control point is a value obtained when the oxygen sensor element is tested after a durability test with a burner combustion gas at 900° C. for 100 hours.

18. An oxygen sensor element which comprises the oxygen sensor of claim 16.

19. An exhaust gas purification system which comprises the oxygen sensor of claim 18.

20. The oxygen sensor element according to claim 2, wherein said part formed of the nonstoichiometric compound is disposed on a second porous coated layer formed of a heat-resistant metal oxide which is disposed on said detection gas side electrode.

21. The oxygen sensor element according to claim 2, wherein said part formed of the nonstoichiometric compound extends over the sensor element except for a distal end portion of the sensor element, the distal end portion having a length of ⅕ to ½ of the entire length, measured from the distal end, of a portion of the sensor element that is exposed to the detection gas.

22. The oxygen sensor element according to claim 21, wherein said distal end portion is covered by a porous coated layer carrying an oxidizing catalyst free of said nonstoichiometric compound.

23. The oxygen sensor element according claim 22, wherein said porous coated layer covering the distal end portion is thicker than the entire porous coated layer covering the remaining portion.

24. The oxygen sensor element according to claim 23, wherein said part formed of the nonstoichiometric compound of said first porous coated layer is disposed on a second porous coated layer.

25. The oxygen sensor element according to claim 22, wherein said porous coated layer carrying the catalyst at the distal end portion has a double porous coated layer structure formed of a primary porous coated layer and an outer porous coated layer.

26. The oxygen sensor element according to claim 25, wherein the oxidizing catalyst is carried on the surface of the outer porous coated layer.

27. The oxygen sensor element according to claim 1, wherein said first porous coated layer is disposed on a second porous coated layer which is disposed on said detection-gas-side electrode.

* * * * *